United States Patent
Torti (10) Patent No.: US 8,744,147 B2
(45) Date of Patent: Jun. 3, 2014

(54) GRAPHICAL DIGITAL MEDICAL RECORD ANNOTATION

(76) Inventor: Robert Torti, Frisco, TX (US)

(*) Notice: Subject to any disclaimer, the term of this patent is extended or adjusted under 35 U.S.C. 154(b) by 939 days.

(21) Appl. No.: 12/485,630

(22) Filed: Jun. 16, 2009

(65) Prior Publication Data

US 2010/0316276 A1    Dec. 16, 2010

(51) Int. Cl.
*G06K 9/00*    (2006.01)

(52) U.S. Cl.
USPC ........... 382/128; 382/100; 382/285; 382/294; 705/2; 705/3; 705/4; 715/200; 715/273

(58) Field of Classification Search
None
See application file for complete search history.

(56) References Cited

U.S. PATENT DOCUMENTS

| | | | |
|---|---|---|---|
| 5,179,651 A * | 1/1993 | Taaffe et al. | 345/555 |
| 5,557,785 A | 9/1996 | Lacquit et al. | |
| 5,581,460 A * | 12/1996 | Kotake et al. | 705/3 |
| 5,894,338 A | 4/1999 | Miehle et al. | |
| 6,132,218 A | 10/2000 | Benja-Athon | |
| 6,307,573 B1 | 10/2001 | Barros | |
| 6,366,683 B1 | 4/2002 | Langlotz | |
| 6,819,785 B1 | 11/2004 | Vining et al. | |
| 7,362,334 B2 | 4/2008 | Daignault, Jr. | |
| 7,793,217 B1 * | 9/2010 | Kim et al. | 715/255 |
| 7,818,041 B2 * | 10/2010 | Kim et al. | 600/407 |
| 7,949,542 B2 * | 5/2011 | Hamiter et al. | 705/2 |
| 2002/0021828 A1 | 2/2002 | Papier et al. | |
| 2003/0016850 A1 * | 1/2003 | Kaufman et al. | 382/128 |
| 2003/0184544 A1 | 10/2003 | Prudent | |
| 2005/0107690 A1 * | 5/2005 | Soejima | 600/425 |
| 2006/0025670 A1 * | 2/2006 | Kim et al. | 600/407 |
| 2006/0242149 A1 * | 10/2006 | Richard | 707/8 |
| 2008/0136838 A1 | 6/2008 | Goede et al. | |

OTHER PUBLICATIONS

Caruso et al. Image Annotation with Adobe Photoshop, 2002, Journal of Digital Imaging, vol. 15, No. 4, pp. 197-202.*
Wolfe, Annotation technologies: A software and research review, 2002, Computers and Composition ,19, pp. 471-497.*
Goede et al. A Methodology and Implementation for Annotating Digital Images for Context-appropriate Use in an Academic Health Care Environment, Feb. 2004, Journal of the American Medical Informatics Association vol. 11 No. 1.*
Lober et al. , IML: An Image Markup Language, 2001, AMIA.*
Cai et al. Web-Based Digital Medical Images, 2001, IEEE Computer Graphics and Applications, pp. 44-47.*
Adobe Systems Incorporated, Adobe Acrobat Professional 8 Guide, 2006, pp. 1-5, 33-47, 62.*
http://www.oisi.com/index.php?option=com_content&view=article&id=240&Itemid=176.
http://www.oisi.com/index.php?option=com_content&view=article&id=252&Itemid=188.

* cited by examiner

*Primary Examiner* — Matthew Bella
*Assistant Examiner* — Jason Heidemann
(74) *Attorney, Agent, or Firm* — Young, Basile, Hanlon & MacFarlane, P.C.

(57) ABSTRACT

Disclosed herein is a method for graphically representing the condition of an anatomical structure that is the subject of a medical examination. The method includes displaying a background image representative of the anatomical structure, the image including a plurality of layers corresponding to different layers of the anatomical structure, selecting a layer of the background image, presenting a plurality of symbols, each corresponding to an anatomical pathological state and selected from a group associated with the selected layer, each symbol having a plurality of parameters which determine the rendering condition of a symbol on the background, selecting one of the presented symbols, selecting an X-Y position within the selected layer and displaying the symbol on the selected layer.

20 Claims, 7 Drawing Sheets

GRAPHICAL DIGITAL MEDICAL RECORD ANNOTATION

FIELD OF THE INVENTION

The present invention pertains generally to digital medical record software.

BACKGROUND

Medical records can contain a wide variety of information such as patient demographics, visual and medical history, diagnoses and treatments. Many hospitals and medical providers create and store this body of information in paper charts. Some hospitals and medical providers are gradually replacing paper charts with digital medical records in order to, for example, reduce medical errors, improve efficiency and reduce healthcare costs.

Digital medical record software presently available can permit a user to enter a patient's medical information through, for example, selection of a descriptive sentence from a drop-down list or manual user entry. Drop-down lists have predetermined entries and may not provide complete or accurate medical information. If additional information needs to be entered, it may be necessary for the user to enter the text manually. However, entering long text entries can be time-consuming and can be difficult to process.

Additionally, some digital medical record software can permit the creation of pixel-based drawings. A user can view these pixel-based drawings and can, for example, attain a personal understanding of a medical condition. However, apart from their illustration, digital medical record software may be unable to extract information from these pixel-based drawings.

SUMMARY

Embodiments of a method for graphically representing the condition of an anatomical structure that is the subject of a medical examination are disclosed herein. In one such embodiment, a method includes displaying a background image representative of the anatomical structure. The image includes a plurality of layers corresponding to different layers of the anatomical structure. The method also includes selecting a layer of the background image and presenting a plurality of symbols. Each symbol corresponds to an anatomical pathological state and is selected from a group associated with the selected layer. Each symbol has a plurality of parameters which determine the rendering condition of a symbol on the background. Further, the method includes selecting one of the presented symbols, selecting an X-Y position within the selected layer and displaying the symbol on the selected layer.

In another such embodiment, a method includes displaying a background image representative of the anatomical structure. The image includes at least one layer corresponding to an anatomical layer of the anatomical structure. The method also includes selecting one of the at least one layer of the background image and presenting a plurality of symbols. Each symbol corresponds to an anatomical pathological state and is selected from a group associated with the selected layer. Further, the method includes selecting one of the presented symbols. The selected symbol modifies the background image, and the modification represents a pathological state of the anatomical structure.

Other embodiments of the invention are described in additional detail hereinafter.

BRIEF DESCRIPTION OF THE DRAWINGS

The description herein makes reference to the accompanying drawings wherein like reference numerals refer to like parts throughout the several views, and wherein.

DETAILED DESCRIPTION

Disclosed herein are embodiments of a digital medical record (DMR) software program that permits medically relevant information to be entered, used and stored by a medical provider. Embodiments of the DMR software program can improve the efficiency of the medical provider while permitting the accurate depiction and recordation of medical pathology. Embodiments of the DMR software program permit information to be organized and extracted for use by the medical provider, a patient, a payment provider or any third party.

Figure 1:
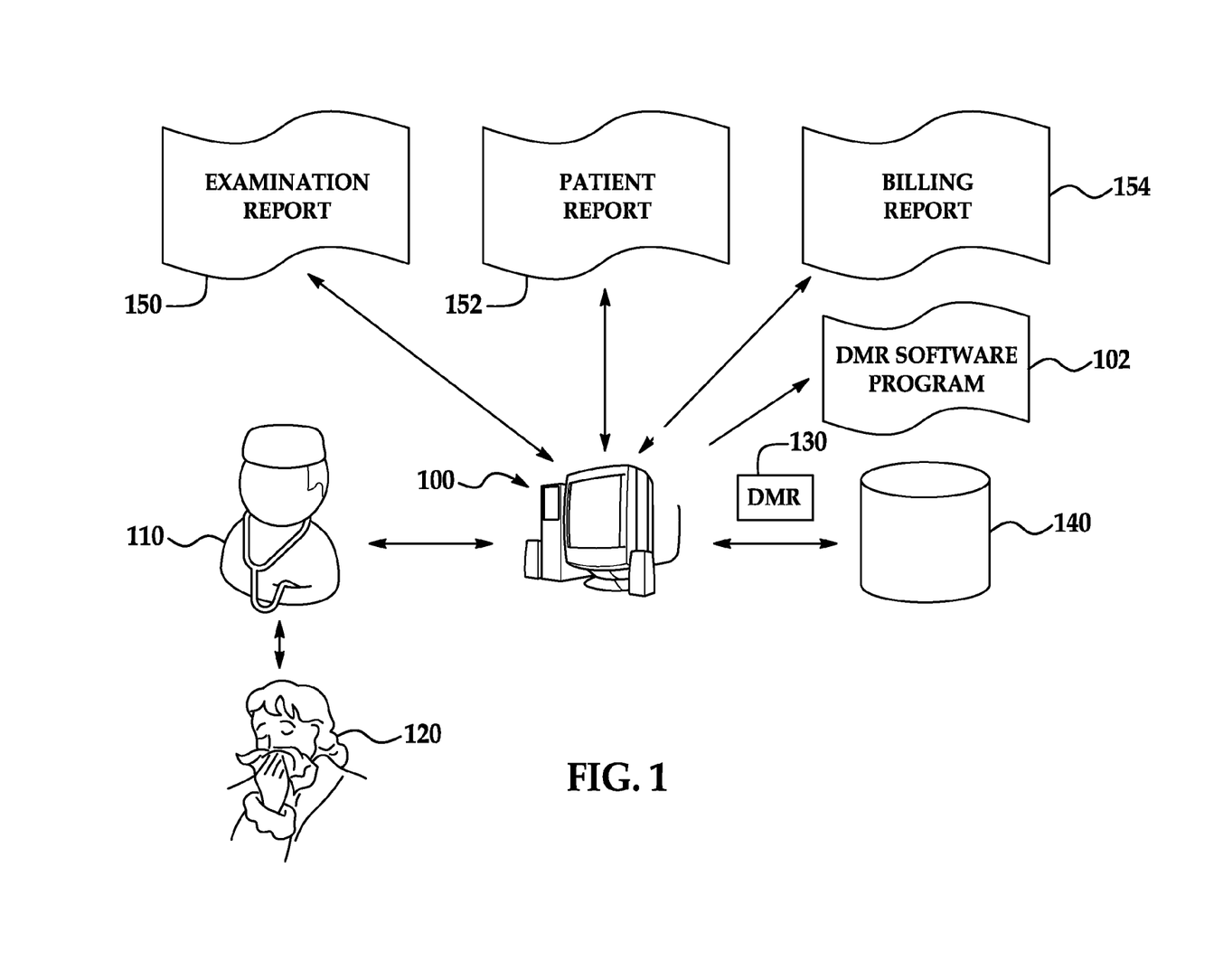
FIG. 1 is a flow diagram for entering a patient encounter into a computer containing a digital medical record (DMR) software program in accordance with one embodiment of the present invention.

FIG. 1 is a flow diagram for entering a patient encounter into a medical provider computer 100 containing a DMR software program 102. DMR software program 102 can provide, as discussed herein, functionality for graphically representing the condition of an anatomical structure that is the subject of a medical examination based on information entered by a medical provider 110.

Medical provider 110 can obtain the information from a patient 120 by, for example, interviewing patient 120, examining patient 120, performing a test on patient 120, performing a procedure on patient 120 or any other suitable method. Medical provider 110 can enter the information about patient 120 into medical provider computer 100 using, for example, any suitable type of computer input peripheral (not shown). Based on the information obtained, DMR software program 102 can create a DMR 130 and store the DMR in a database 140. Database 140 can be any type of memory or storage device and be implemented internally or externally to medical provider computer 100.

Once a DMR 130 has been created for patient 120, medical provider 110 can electronically view and/or modify DMR 130. Software program 102 can also be used to generate an examination report 150, a patient report 152, a billing report 154 or any other report as desired or required.

Medical provider 110 can be a physician, surgeon, dentist, chiropractor, optometrist, psychologist, nurse, therapist pharmacist or any other person. The anatomical structure can be any bone, tissue, organ, muscle cartilage or any other part of any human or non-human being. One non-limiting example of an anatomical structure is an eye. The medical examination can be a physical exam, a mental exam, a procedure, a test, an evaluation or any other scenario. The medical examination can be related to the physical health, mental health, visual health, oral health or cosmetic appearance of patient 120

Medical provider computer 100 can be a laptop computer, a desktop computer, a workstation, a handheld device, a server, a cluster of computers or other any suitable computing device. Software program 102 can be locally-installed on medical provider computer 100, be located on a separate computer server and connected to medical provider computer though, for example, a private access connection (e.g. local area network), or be an application embedded in and accessible through a web server via the Internet. Medical provider 110 can also use medical provider computer 100 to interact with software program 102 by any other suitable method.

Medical provider 110 can access medical provider computer 100 directly, or can operate a device that communicates with medical provider over a network such as the Internet, a wide area network, a local area network, a virtual private network or any other network connection. If communication is indirect, medical provider 110 access the networks utilizing any wired and/or wireless transmission methods. Patient 120 can be a human, animal, or any other being for which a DMR can be created.

The following description and related figures will contain references to exemplary user interface screens of DMR software program 102. The description and related figures reference use of the software in the field of ophthalmology. However, reference to this field is merely exemplary and is not to limit the scope of embodiments of the invention. Those skilled in the art will realize that the teachings described herein may be used in other various fields, such as dentistry. Other embodiments may implement the DMR software program in the context of other fields.

Figure 2:
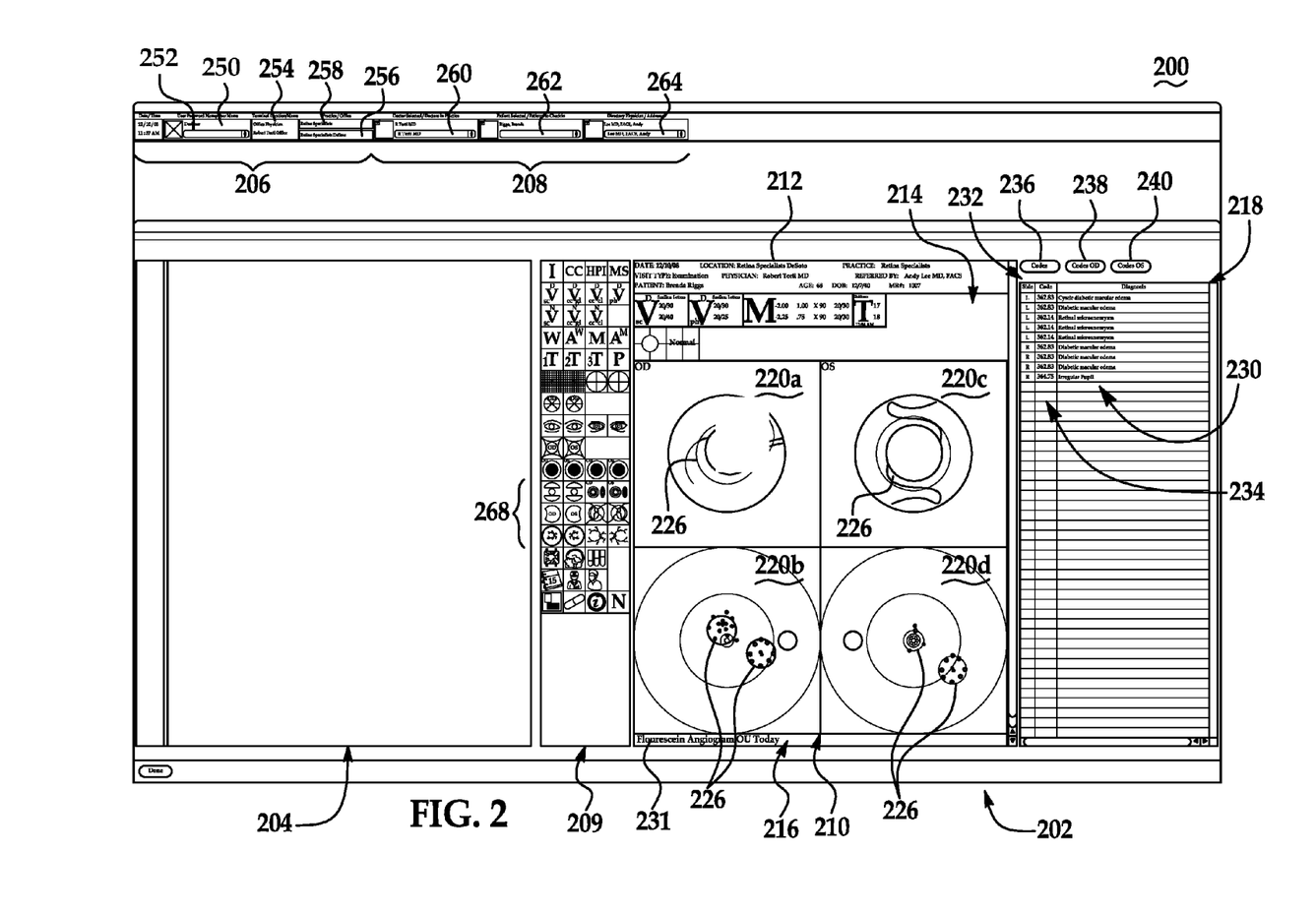
FIG. 2 is an exemplary user interface patient encounter screen of the DMR software program of FIG. 1.

FIG. 2 illustrates an exemplary patient encounter user interface screen 200 of the software program 102 that medical provider 110 can use to, for example, electronically create, view and modify DMR 130 of patient 120. DMR software program 102 can be used to graphically represent the pathological condition of an anatomical structure. Encounter screen 200 can include a present encounter section 202, a previous encounter section 204, a user information bar 206, a filter selection bar 208 and a toolbar 209. Present encounter section 202 can include an exam components section 210, patient information bar 212, a visual test results section 214, an data display section 216 and a diagnosis section 218.

Exam components section 210 can include one or more two-dimensional backgrounds 220. As show in FIG. 2, exam components section 210 includes four backgrounds 220A, 220B, 220C and 220D. Background 220A is, for example, the anterior segment of the right eye and background 220B is, for example, the fundus of the right eye. Similarly, for example, background 220C is the anterior segment of the left eye and background 220D is the fundus of the left eye. Other backgrounds representing other anatomical structures are also available. Any number of backgrounds can be represented on encounter screen 200 as desired or required.

Each background 220 can represent an anatomical structure or part of an anatomical structure and can be composed of one or more layers (not shown). Each layer can represent, for example, an anatomical layer of the anatomical structure. Layers can represent an external layer or an internal of the anatomical structure. Additionally, one or more layers can be a text layer. Other types of layers are also available. These layers can be invisible to medical provider 110. However, in other embodiments, background 220 can be composed of layers that are visible to medical provider 110 or include a combination of visible and non-visible layers.

In operation, medical provider 110 can use toolbar 209 to select background 220 by for example, clicking on the specific background icon desired. Once background 220 has been selected, a dialog box (not shown) can be presented to medical provider 110 to provide, for example, one or more formats for entering information in exam components section 210. These formats can be free text entry, selection of data from a predetermined list, or selection of one or more symbols 226. Other suitable methods of entering information are also available and the embodiments are not limited to entry of information through a dialog box.

To indicate the presence or absence of pathology on the background representing the anatomical structure, medical provider 110 can select one or more symbols 226 for placement on background 220. Each layer can contain any number of symbols 226 that indicate the presence or absence of pathology. When symbols 226 are placed on layers, the location and parameters associated with each symbol 326, as discussed in more detail below, can be recorded in memory as part of DMR 130 of patient 120. The layers can be used for, for example organizing and drawing symbols 226 on each background 200.

Symbols 226 can correspond to, for example, an anatomical pathological state of the anatomical structure. For example, symbols 226 can represent diabetic macular edema. Further, although symbols 226 generally represent an indication of a pathological state, symbol 226 can also indicate absence of pathology in the anatomical structure. Symbol 226 can also represent a text entry, an audio entry or any other visible or non-visible mark that can convey any type of information. Symbols 226 can also have permanent and/or modifiable parameters, which will be discussed in more detail below relating to how and where a symbol is drawn (i.e. the rendering condition) on layers 224 or background 220. Further, symbols 226 are not limited to those presently available in software program 102. Software program 102 may permit the creation of new symbols 226 to represent other pathological states or normal anatomical states.

Each symbol 226 can be selected from a list of icons which represent the symbol. Software program 102 can place symbol 226 at an X-Y position within the selected layer. The X-Y position can be determined either by medical provider 110, or based on the symbol's parameters, by software program 102. As will be discussed in more detail below, once symbol 226 is placed on background, it can be further manipulated.

Each symbol 226 can be associated with medical data or information, based on, for example, predetermined information associated with the symbol or additional manipulation of symbol 226 using the symbol's parameters. Some examples of predetermined information associated with the symbol can include a text descriptor of the symbol, diagnostic codes, procedure codes or billing information. In other embodiments, this information can be modified by, for example, medical provider 110 or software program 102.

Accordingly, exam components section 210 of DMR software program 102 permits a pseudo three-dimensional space to be created using layers in conjunction with one of the backgrounds 220 that represents the anatomical structure or part of the anatomical structure. The layers can allow representation of a plurality of anatomical pathological states through selection and display of intelligent symbols 226. In alternative embodiments, exam components section 210 can illustrate anatomical structure as a 3-dimensional graphic.

Backgrounds 220, layers and symbols 226 can be created using scalar vector graphics. Each graphical entity can be composed of graphic primitives and text. Primitives can include lines, circles, ovals, rectangles, curves and any other suitable geometric object. Each primitive can have graphical parameters such as line thickness, color, fill, filters and any other graphical parameter.

Further, software program 102 permits backgrounds, layers and symbols to be designed for any field or specialty. Further, software program 102 can be customized so as so accommodate the preferences of medical provider 110. Backgrounds, layers, and symbols can be created and deleted as required or desired.

As discussed herein, software program 102 permits the creation of intelligent symbols 226 with various parameters and the parameters can determine the rendering condition of the symbol on background. Software program 102 permits medical provider 1130 to create DMR 130 of a patient encounter on the fly. In turn, DMR 130 can include anatomically correct and medically relevant information without, for example, the use of predefined templates. Further, software program 102 permits medical provider 110 to quickly and efficiently enter data (e.g. drag-and-drop of symbol) pertaining to the patient encounter. In turn, the data entered in the program can provide, for example, complete diagnostic, documentation and billing information. Each symbol 226 placed on background 220 can encapsulate specific diagnostic, documentation and billing data related thereto and can prevent medical provider 110 from entering redundant data into the software program. Accordingly, medical provider 110 can be efficient without comprising the accuracy and completeness of DMR 130.

Figure 3:
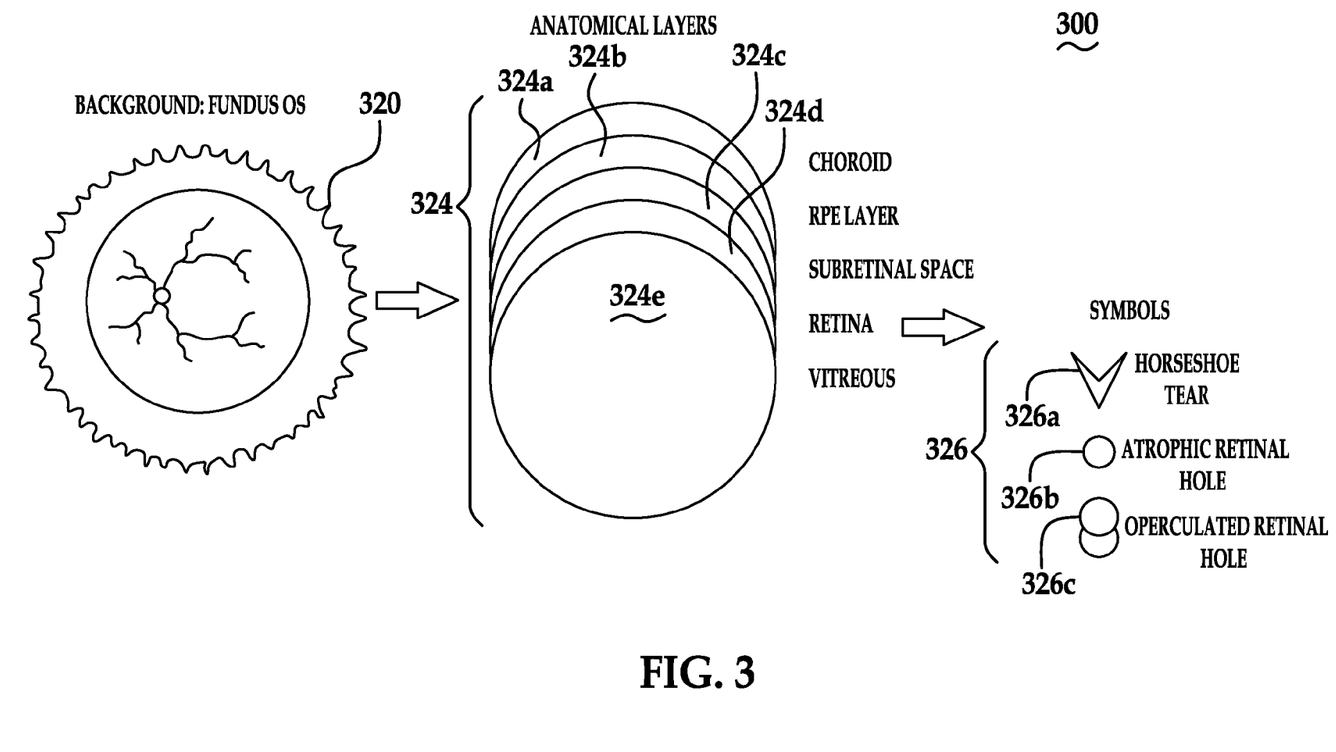
FIG. 3 is a schematic diagram illustrating an exemplary relationship between a background, anatomical layers and symbols used in the DMR software program of FIG. 1.

FIG. 3 illustrates a relationship diagram 300 of an exemplary background 320, exemplary layers 324 and exemplary symbols 326. Background 320 represents the fundus of the left eye. Background 320 can be composed of, for example, five layers designated as choroid 324a, RPE 324b, subretinal space 324c, retina 324d and vitreous 324e. These five layers 324 represent anatomical layers of the fundus of the left eye. Each layer 324a-e can have symbols 326 that, as discussed previously, correspond to an anatomical pathological state of the anatomical structure. Accordingly, for example, horseshoe tear 326a, atrophic retinal hole 326b and operculated retinal hole 326b can be associated with layer 324d.

As such, a different set of symbols 326 can be associated with each of the layers 324. In alternative embodiments, the same set of symbols 326 can be assigned to each layer 324. In other embodiments, some backgrounds may not have any symbols assigned to one or more of the layers.

Returning to FIG. 2, patient information bar 212 can contain information related to the present encounter with patient 120. For example, patient information bar 212 can include the date, the location, the practice, the type of visit (e.g. examination, procedure, test, etc.), the physician name, the referring physician name, the medical record (MR) number, and the name, age and date of birth of patient 120. Medical provider 110 can enter information for display on patient information bar 212 by using icon(s) in toolbar 209, as will be discussed in more detail below.

Visual test results section 214 can contain information related to any type of eye examination such as an exam for visual acuity or pupil function. Other examinations are also available. Medical provider 110 can enter the results from the eye examination using icons in toolbar 209, as discussed in more detail below, for performing visual tests. For example, medical provider 110 can use the 'P' icon to enter the results from testing the pupil function of patient 120. The results may be entered, for example, using a pop-up dialog box (not shown). The pop-up dialog box can have predefined fields, which permit medical provider 110 to enter information pertaining to each of the eye examinations. Information can also be entered by any other suitable methods.

Data display section 216 can contain information related to orders for tests and procedures by medical provider 110. For example, medical provider 110 can use icons, as discussed below, of toolbar 209 to order a diagnostic test to be performed on patient 120 and indicate the anatomical structure that the test is to be performed and further indicate when the test is to be performed. For example, as illustrated in FIG. 1, data display section 216 can display a test entry 231 such as 'Fluorescein Angiogram OU Today' indicating that a fluorescien angiogram is ordered on both eyes (OU) of patient 120. Any number of test entries can be entered into order 216. Data display section can also display any other information related to the patient encounter such as dictation or doctor referrals.

Diagnosis section 218 can contain a list of diagnoses 230 for the present patient encounter. Once a symbol 226 has been placed on a background 220, the diagnosis corresponding to the symbol can automatically be added to list 230. In other embodiments, the diagnosis can be entered from a list or by any other suitable method. Diagnosis section 218 can contain a text description 230, a side 232 (e.g., left, right, neither, both) and a code 234. Code 234 can be associated with the IDC9 diagnostic coding system. Diagnosis section 218 can also contain any other identifying information about the anatomical structure being examined as desired or required. Accordingly, automatically adding a billing code to diagnoses 230 once symbol 226 has been added to background 220 permits accurate patient and insurance billing. Each symbol 226 can also reference other coding systems. In some instances, symbol 226 may not be associated with any code.

Medical provider 110 can also filter the diagnoses to be displayed in diagnosis section 218. For example, to view all diagnoses, medical provider 110 can select 'Codes' button 236. To view diagnoses associate with a particular side, medical provider 110 can select 'Codes OD' button 238 to view diagnosis associated with the right eye and can select 'Codes OS' button 240 to view diagnoses associated with the left eye. Other filtering mechanisms are also available.

Medical provider 110 can view previous encounters (none shown) for patient 120 in previous encounter section 204. Previous encounters may be those electronically created by software program 102, paper medical records that have been digitally uploaded, electronic medical records imported from another electronic medical record program or any other record of previous encounter for patient 120.

User information bar 206 contains information about the user (e.g. medical provider) entering information into exemplary encounter screen 200. When medical provider 110 launches DMR software program 102, they can enter login information including, for example, a user name and password into fields 250 and 252 to successfully view information pertaining patient encounters. Other embodiments may not compel the user to enter login information. Field 254 can indicate the terminal location and terminal name of the computer attempting to use DMR software program 102. Field 256 can indicate the practice name of medical provider 110 and field 258 can indicate the office name where the practice is located. Other information related to the user of software program can be displayed and organized as desired or required.

Once medical provider 110 has successfully launched and logged in to the DMR software program 102, filter selection bar 208 can be used to select a DMR to be displayed on encounter screen 200. Accordingly, medical provider 110 can filter by doctor using field 260, by patient using field 262 or by directory physician by field 264. If, for example, there is more than one DMR for a filter selection, a record can be display a list of DMR that satisfy the filter selection. Other filtering mechanisms are also available. For example, encounter screen 200 may only display DMRs of patients who are to be examined on a particular day. If there is no record for a DMR for a patient, medical provider 110 can create a new DMR.

Once DMR 130 is displayed for patient 120, medical provider 110 can use background icons 268 to select background 220 for display in exam components section 210. Medical provider 110 can select background 220 by, for example, clicking one of background icons 268. In other embodiments, medical provider 110 can select background 220 by dragging-and-dropping one of background icons 268, double-clicking one of icons 268 or any other suitable method. Once a background 220 has been selected, as discussed previously, medical provider 110 can be presented with a dialog box to enter information to graphically represent pathological or normal states of the anatomical structure.

Figure 2A:
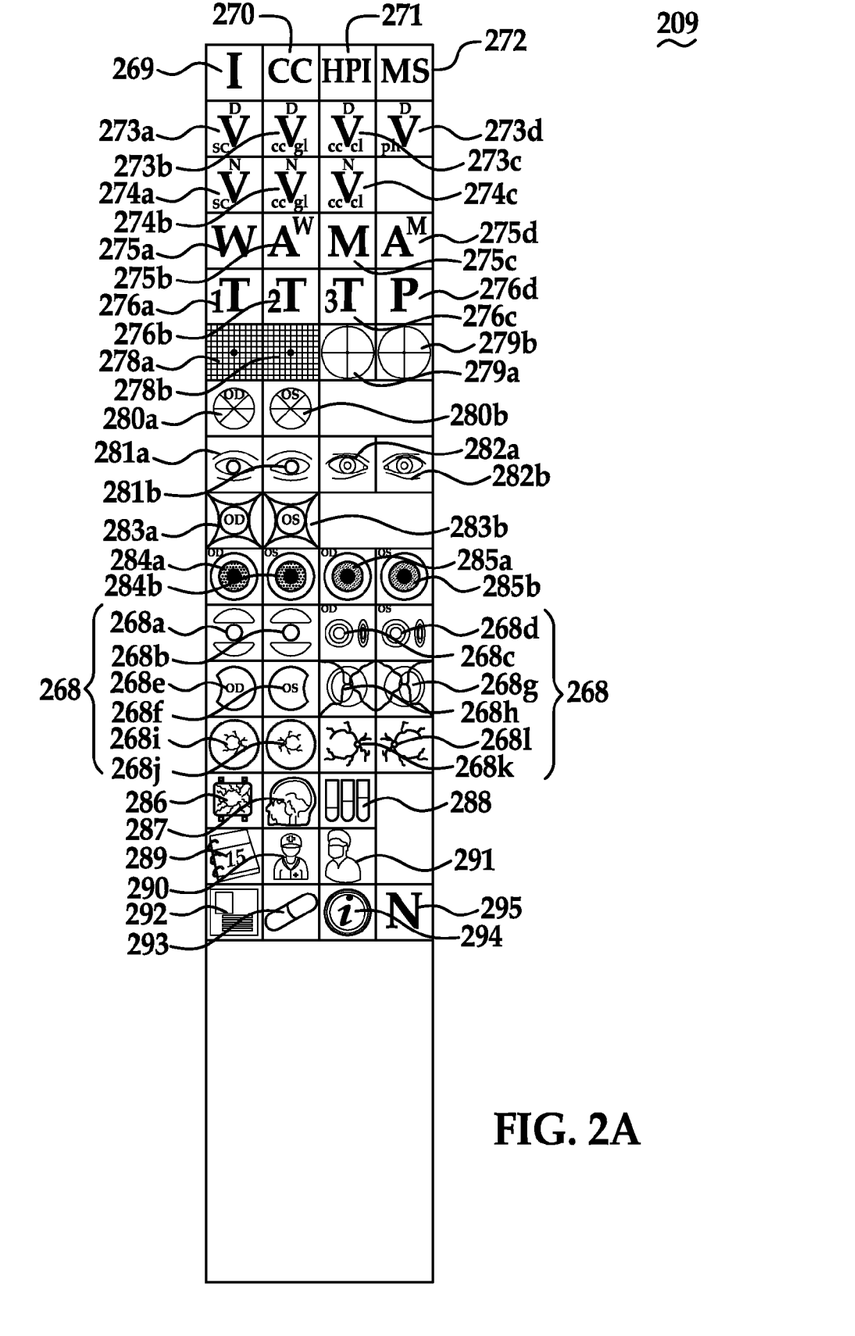
FIG. 2A is an enlarged view of an exemplary tool/bar used in the user interface patient encounter screen of FIG. 2.

FIG. 2A is an enlarged view of toolbar 209 used in the user interface patient encounter screen of FIG. 2. As discussed in more detail below, the icons can correspond to various sections of patient encounter 200 to enter or modify data related to, for example, patient demographics, exam components (e.g. backgrounds 220), orders for tests and procedures, appointments, referrals, dictation, and medication changes.

Toolbar 209 can include a patient information icon 269, a chief complaint icon 270, a history present illness icon 271 and a mental status icon 272. Toolbar 209 can also include icons to input or view information related to visual examinations such as a vision distance without correction icon 273a, a vision distance with correction icon 273b, a vision distance with contact lens icon 273c, a vision distance with pinhole icon 273d, a vision near without correction icon 274a, a vision near with glasses icon 274b, a vision near with glasses icon 274c. Information input using icons 273 and 274 can be displayed in visual test results section 214. Further, toolbar 209 can include icons to input or view information about past, present or future prescriptions such as a present glasses prescription icon 275a, a present add prescription icon 275b, a new prescription icon 275c and a new add prescription icon 275d.

Other types of examinations are also available and may have icons associated with the examination so that medical provider may input or view information related to the specific examination. For example, toolbar 209 can include an intraocular pressure 1 icon 276a, an intraocular pressure 2 icon 276b, an intraocular pressure 3 icon 276c, a pupil function icon 277, an amsler grid right icon 278a, an amsler grid left icon 278b, a confrontation visual field right icon 279a, a confrontation visual field left icon 279b, an extraocular motility right icon 280a, an extraocular motility left icon 280b, a simple external exam right icon 281a, a simple external exam left icon 281b, a complex external exam right icon 282a, a complex external exam left icon 282b, a gonioscopy right icon 283a, a gonioscopy left icon 283b, a simple slit lamp exam right icon 284a, a simple slit lamp exam left icon 284b, a complex slit lamp exam right icon 285a and a complex slit lamp exam left icon 285b.

As discussed previously, medical provider 110 can select a background icon 268 in order to display the background associated with the specific icon in exam components section 210. Examples of background icons are a conjunctiva right icon 268a, a conjunctiva left icon 268b, a lens right icon 268c, a lens left icon 286d, a vitreous right icon 268e, a vitreous left icon 268f, an optic nerve right icon 268g, an optic nerve left icon 268h, a fundus right icon 268i, a fundus left icon 268j, a macula right icon 268k and a macula left icon 268l.

Toolbar 209 can also include additional icons that facilitate the creation of DMR 130 and the encounter between medical provider 110 and patient 120. Accordingly, toolbar 209 can include a diagnostic procedures office icon 286, a diagnostic procedures elsewhere icon 287, an order lab tests icon 288, a follow-up appointment icon 289, a referral icon 290, a procedures office icon 291, a dictation list icon 292, a prescribing medications icon 293, a patient instructions/warnings icon 294 and a notes icon 295.

Referring again to FIGS. 1 and 2, when examination report 150 is created by software program 102, it can obtain this information stored in memory and can include the backgrounds 220, which medical provider has selected and modified using symbols 226. Accordingly, examination report 150 can be generated so that it produces a report of only those backgrounds 220 that medical provider has modified. In alternative embodiments, examination report can contain any other information including a list of all backgrounds regardless of whether they have been modified.

Similarly, software program 102 can use information DMR 130 of patient 120 to create a patient report 152 for, for example, the referring physician. Patient report 152 can inform the referring doctor of the presence or absence of pathology in the anatomical structure that was the subject of the medical examination. Software program 102 can use parameters associated with symbols 226, (e.g. descriptor and procedure code) that have been placed on the background 220 to generate patient report 152 in a format suitable for the referring doctor. For example, patient report 152 can be generated in a dictation style format. Other formats are also available. In other embodiments, patient report 152 can be sent to patient 120 or any other person that desires or requires information pertaining to the medical examination of patient 120.

Software program 102 can also use information DMR 130 of patient 120 to create billing report 154. Software program 102 can use parameters associated with symbols 226, (e.g. billing code and a descriptor) that have been placed on the background 220 to generate a billing report in a format suitable for submission to a payment provider. The level of billing to, for example, a patient or payment provider, can be determined by the number and type of backgrounds 226 selected and modified.

For example, backgrounds 220 can be assigned a value, which represents a billing level. Software program 102 can accumulate these values from each background 200 added by medical provider 110 in order to determine a billing level. Once a present encounter is completed, the software can modify a code, such as a CPT code, to correspond to the appropriate level of billing. Other methods of determining the level of billing are also available.

Figure 4:
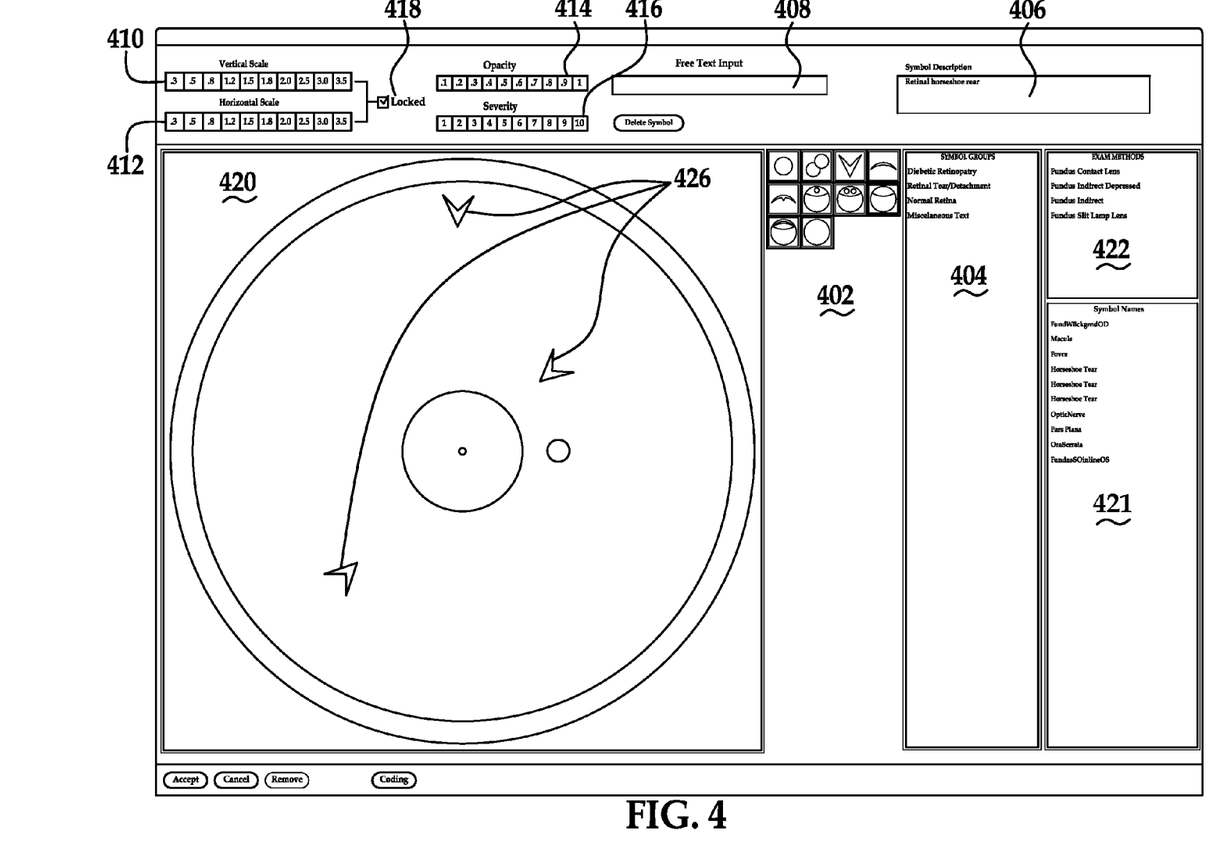
FIG. 4 is an exemplary user interface background modification screen of the DMR software program of FIG. 1.

FIG. 4 illustrates an exemplary background modification user interface screen 400 of the software program 102 that medical provider 110 can use to, for example, modify a background 420 by assigning one or more symbols 426 to background 420. A selection of symbols can be presented to medical provider 110 on a toolbar 402.

Symbols 426 can be grouped by, for example, similar pathological conditions. A user of software program 102 can define different groups and can assign different symbols to each group. The layers assigned to a background determine which symbols are available to medical provider 110 in background modification screen 400.

In other embodiments, symbols will not be grouped and all symbols can be presented to medical provider 110 or if grouped, symbols can be grouped using any other organizational technique. One such technique may be grouping symbols by their frequency of use. A list of groups 404 can be displayed on modification screen 400 showing the names of the groups that contain symbols 426 that are available for selection.

Software program 102 can place symbols 426 on the background in an order determined by the layer to which they belong. The layers can be ordered back to front and can correspond to the proper anatomical layering as viewed by medical provider 110. For example, symbols 426 present on the back layers can be drawn before symbols present on the front layers. Accordingly, symbols 426 can be organized in an anatomical fashion. Further, for example, within a layer, symbols can be drawn from the largest to the smallest. This can prevent a smaller symbol from being covered by a larger symbol. In other embodiments, symbols 426 can be placed on layers in any order. The location of each symbol 426 can be recorded in memory.

Symbols 426 can also have varying levels of transparency. Transparency can assist in preventing a symbol from obscuring anatomical details of an underlying symbol. Further, for example, transparency can also convey the severity level of a pathological condition.

To represent normal or pathological changes to background 420, medical provider selects one of the symbols from selection of symbols 402. Once a symbol is selected from toolbar 402, a description of the symbol, such as the symbol name, can be displayed in field 406. Each symbol 426 can be a graphical symbol or text. Graphical symbols can be inserted using toolbar 402 and text symbols can be inserted by typing text into free text input field 408.

Once one or more symbols 426 have been selected and placed on background 420 9, the symbol can be manipulated using vertical 410, horizontal scale 412, opacity scale 414 and severity scale 416. These scales can determine how symbols 426 are drawn. Vertical scale 410 and horizontal scale 412 determine the vertical size and horizontal size, respectively of symbol 426 on background 420. The scale can be defined in, for example, pixels per millimeter. Other scaling sizes are also available. The vertical scale 410 and horizontal scale 412 for a symbol can be locked by checking or unlocked by unchecking cheekbox 418.

A list 421 can display the names of each of the symbols that have been placed on background 420. Additionally, list 421 can also display the names of background 420, layers of background 420 and any other symbol associated with background 420. A list 422 can display the exam methods that can be used to examine each of backgrounds 420.

Backgrounds can further divided into zones corresponding to predefined areas of the background image. Zones are invisible shapes which can influence any symbol which is placed within it. The zone can indicate an anatomical location of the anatomical structure. Further, the zone may influence the symbol by changing a code (e.g. billing or procedure) associate with the symbol, changing a medical treatment associated with the pathological state as represented by the symbol, change text associated with the symbol or may change any other information associated with the symbol. Placing a symbol within a zone may also permit additional modifications of the symbol.

Figure 5:
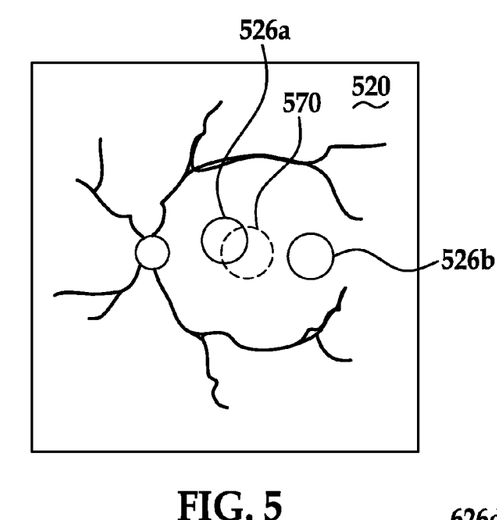
FIG. 5 is a schematic diagram illustrating an exemplary zone in a background.

FIG. 5 illustrates an exemplary background 520 representing the Macula OS and utilizing a zone 570. Background 520 includes symbols 526a and 526b for diabetic macular edema and a zone 570. Zone 570 can be, for example, a circular region, centered on the fovea and representing a 500 micron radius. Zones can also be any other shapes, sizes or have any other location on background 520. Symbol 526a falls within zone 570 whereas symbol 526b does not fall within zone 570. Accordingly, the macular edema pathology represented by symbol 526a may require medical treatment using a focal laser whereas the macular edema pathology represented by symbol 526b may not require a focal laser. Further, unlike symbol 526b, since symbol 526a is located with zone 570, it can be associated with a proper billing code related to using a focal laser.

The symbols presented to medical provider 110 can have one or more parameters. Each parameter can determine the rendering condition of a symbol on the background. Parameters can include symmetry, positioning, density, severity, scaling, movability, opacity and persistence.

Figure 6:
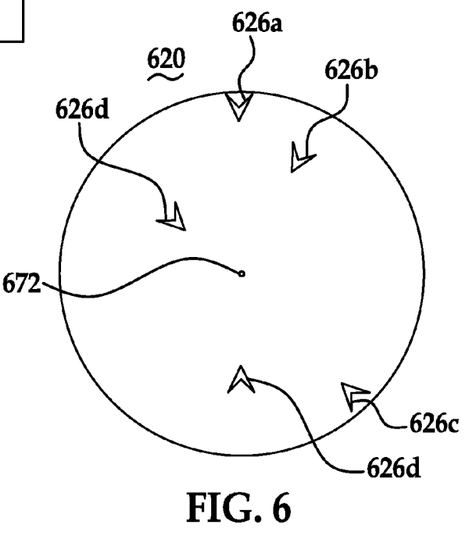
FIG. 6 is a schematic diagram illustrating an exemplary symbol having polar symmetry.

A symbol can have at least one of three types of symmetry: polar, horizontal and vertical. FIG. 6 illustrates an example of symbols 626A-E having polar symmetry. A symbol having polar symmetry can be placed around a point 672 defined in background 620. Point 672 can be visible or invisible. In the example of FIG. 6, point 672 is the center point of background 620. However, point 672 can be any point, line or other reference marking in background 620.

Figure 7:
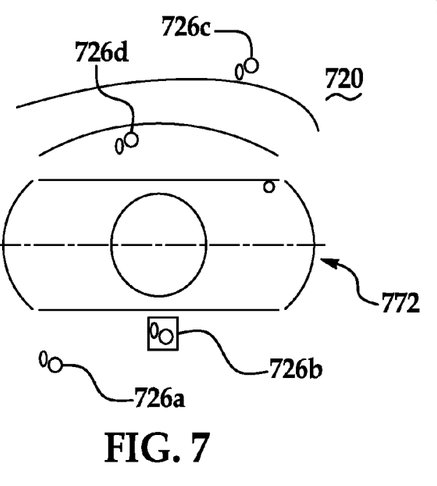
FIG. 7 is a schematic diagram illustrating an exemplary symbol having horizontal symmetry.

FIG. 7 illustrates an example of symbols 726A-D having horizontal symmetry. A symbol having horizontal symmetry can be illustrated around a horizontal symmetry line 772 defined in the middle of background 720. However, horizontal symmetry line 772 is not limited to the middle of background 720 and can be placed in any other location. Horizontal line can be visible or invisible. In the example of FIG. 7, when medical provider 110 drops symbols 726A and 726B having horizontal symmetry, they can be reflected over horizontal symmetry line to additionally display symbols 726C and 726D, respectively. Horizontal symmetry line can act as a mirror and accordingly, symbol 726C can be a mirror image of 726A and symbol 726D can be a mirror image 726B. As discussed in more detail below, symbols can have a fixed vertical position or an unfixed vertical position in relation to the horizontal symmetry line.

Symbols having vertical symmetry are similar to those symbols having horizontal symmetry. Rather than being reflected over a horizontal symmetry line, symbols having vertical symmetry can be reflected over a vertical symmetry line. The vertical symmetry line can be placed at any location of the background. As discussed in more detail below, symbols can have a fixed horizontal position or an unfixed horizontal position in relation to the vertical symmetry line.

Figure 8:
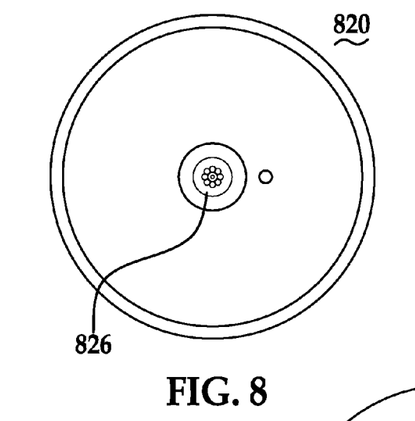
FIG. 8 is a schematic diagram illustrating an exemplary symbol having fixed positioning.

A symbol can have at least one of three types of positioning: fixed, X and Y, and based on symmetry. FIG. 8 illustrates an example of a symbol 826 having fixed positioning. In fixed positioning, symbol 826 appears in a specified position regardless of where it is dropped on background 820. For example, symbol 826 representing cystic edema of the macula can only occur at the center of the retina (i.e. center of background 820). As such, even if medical provider attempt to place symbol 826 at a location other than at the center of background 820, DMR software program 102 can automatically place the symbol in its correct or alternative position based on its parameter of fixed positioning. Fixed positioning can also refer to a fixed vertical position where the symbol is always a predetermined distance from a horizontal reference line or a fixed horizontal position where the symbol is always a predetermined distance from a vertical reference line. Fixed positioning can also include any other mechanism by which the positioning of the symbol is not determined by medical provider 110.

Referring again to FIG. 5, symbols 526a and 526b are examples of symbols having X and Y positioning. Symbols having X (i.e. horizontal) and Y (i.e. vertical) positioning can be placed on the background where the symbol is, for example, dragged-and-dropped by. As discussed previously, a symbol may only have X positioning or Y positioning since its vertical positioning or horizontal positioning may be fixed. In alternative embodiments that for example, containing a 3-dimensional graphic section, a third component Z can be added to denote the depth of the symbol.

Figure 9:
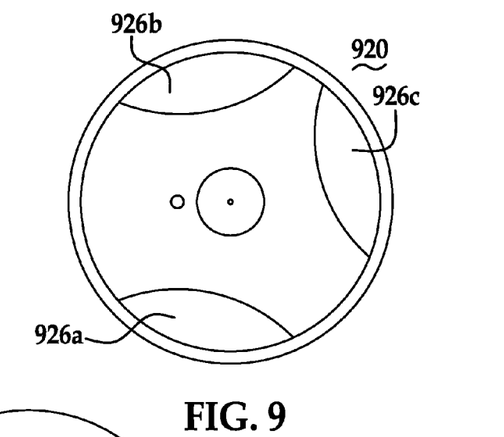
FIG. 9 is a schematic diagram illustrating an exemplary symbol having positioning based on symmetry.

FIG. 9 illustrates an example of a symbol 926a-c having positioning based on symmetry. In particular, the example of FIG. 9 illustrates positioning of a symbol based on polar symmetry. Accordingly, symbols 926a-c can be drawn a predetermined distance from the center of background 920. Symmetry-based positioning can also include positioning a symbol based on horizontal symmetry or vertical symmetry. In horizontal symmetry, the symbol can be drawn a predetermined distance from a vertical symmetry line. In vertical symmetry, the symbol can be drawn a predetermined distance from a horizontal symmetry line.

A symbol may also have varying density levels that can be used to vary the appearance and meaning of a basic symbol. The basic symbol can be the symbol at the lowest density level (e.g. level 1). Additional symbols, similar in appearance to the basic symbol, can be added to the basic symbol when a higher density level is selected, and likewise, symbols can be removed from the symbol when a lower density level is selected. Different density levels can be selected using, for example, severity scale 416 of FIG. 4.

Figure 10:
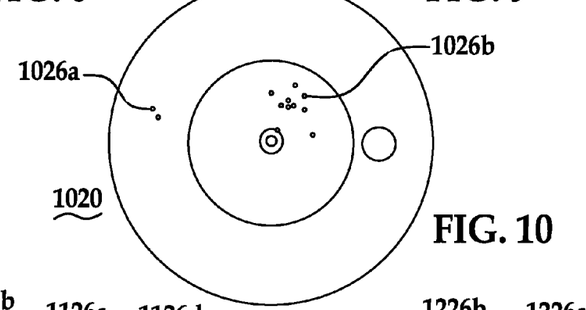
FIG. 10 is a schematic diagram illustrating exemplary symbols having different densities.

FIG. 10 is a schematic diagram illustrating exemplary symbols 1026a and 1026b having different densities. Symbol 1026a can have a density at for example, level 1, whereas symbol 1026b can have a density at, for example, level 7. Accordingly, medical provider 110 does not have to drag-and-drop multiple identical symbols to illustrate a more severe pathological condition. Referring again to FIG. 4, severity scale 416 can be used to vary the density of symbols. Other suitable graphics depicting density levels for other symbols are also available. In other embodiments, medical provider 110 can display different density levels using any other suitable technique. One non-limiting technique is for density levels to be illustrated using different colored symbols.

Symbols having different stages, similar to density, can be used to vary the appearance and meaning of a basic symbol. The basic symbol can be the symbol at the lowest stage level (e.g. level 1). Additional symbols, that can be different in appearance to the basic symbol, can be added to the basic symbol when a higher stage level is selected, and likewise, symbols can be removed from the symbol when a lower stage level is selected. Different stage levels can be selected using, for example, severity scale 416 of FIG. 4.

Figure 11:
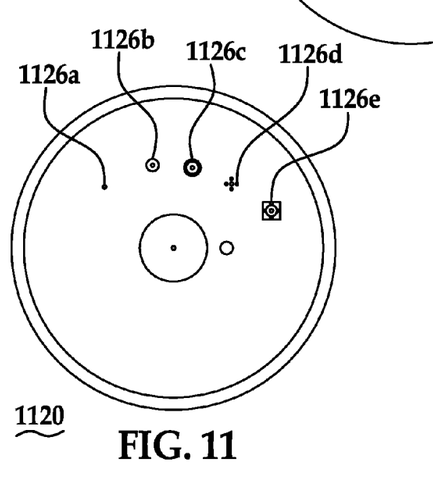
FIG. 11 is a schematic diagram illustrating exemplary symbols having different stages.

FIG. 11 is a schematic diagram illustrating exemplary symbols 1126a-e having different stages. For example, symbol 1126a can have a complexity level at stage 1, symbol 1126b can have a complexity level at stage 2, symbol 1126c can have a complexity level at stage 3, symbol 1126d can have a complexity level at stage 4 and symbol 1126e can have a complexity level at stage 5. Accordingly, medical provider 110 does not have to drag-and-drop multiple symbols to illustrate a more complex pathological condition. Referring again to FIG. 4, severity scale 416 can be used to vary the complexity of symbols. Other suitable graphics depicting stage levels for other symbols are also available. In other embodiments, medical provider 110 can display different stage levels using any other suitable technique. One non-limiting technique is for density levels to be illustrated using different colored symbols.

Further, once a symbol having density or a complex symbol has been placed on a background, in addition to its predetermined description, an additional dictation text line can automatically be associated with the symbol having the modified density or complexity. The dictation text line can include text associated with each density level and each complexity level so that the symbol can be associated with an appropriate descriptor.

Figure 12:
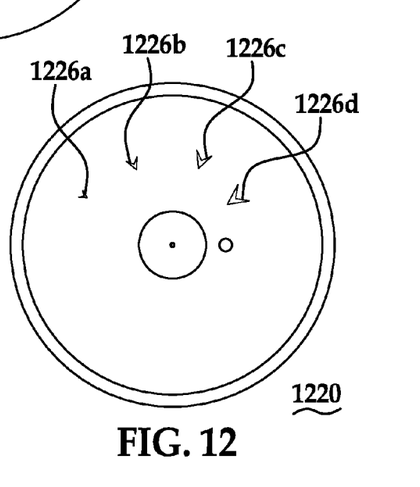
FIG. 12 is a schematic diagram illustrating exemplary symbols having different scales.

FIG. 12 is a schematic diagram illustrating exemplary symbols 1226a-d having different scales. Referring again to FIG. 4, vertical scale 410 and horizontal scale 412 can be used to adjust the vertical size and horizontal size of symbols 1226a-d on background 1220. In other embodiments, the size of symbols can be changed by any other technique. One suitable non-limiting technique is to select the symbol and drag it to the size desired.

Further, different background images may have different scales and a symbol, when selected and placed on the background, can be displayed proportionally to the background image's scale. As such, two backgrounds containing drawn at two different scales may display the same symbol at a different size.

Symbols may or may not, as discussed above with reference to fixed positioning, be movable. Symbol may be movable by selecting the symbol, and dragging it to a desired location on a background.

Additionally, the opacity of a symbol can be modified. Referring again to FIG. 4, opacity scale 414 can be used to adjust the opacity of a symbol from, for example, no opacity to 100% opacity. As discussed previously, a medical provider 110 can, for example, graphically represent the anatomical structure by placing symbols beginning from the most posterior layer to the most anterior layer. Further, when medical provider 110 selects and places a symbol on a posterior layer, medical provider can adjust the opacity (e.g. to less than 100%) so that larger symbols on more anterior layers do not obstruct the view of these symbols on the posterior layers.

Symbols may have also have persistence. If a symbol has persistence and was present on a background previous encounter of patient 120, it can automatically appear on a new background when it is selected by medical provider 110. Accordingly, medical provider 110 may not have to reenter a persistent symbol which was once present.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed:

1. A method for graphically representing the condition of an anatomical structure that is the subject of a medical examination, wherein the anatomical structure includes a plurality of anatomical layers, the method comprising:
    displaying a background image representative of the anatomical structure, the background image including a plurality of image layers such that each anatomical layer in the plurality of anatomical layers corresponds with a respective image layer in the plurality of image layers, wherein displaying the background image includes displaying the plurality of image layers such that a first image layer from the plurality of image layers is superimposed over a second image layer from the plurality of image layers;
    presenting a plurality of intelligent symbols, each intelligent symbol associated with at least one image layer from the plurality of image layers, each intelligent symbol having a plurality of parameters which determine a rendering condition of the respective intelligent symbol;
    identifying a selected symbol from the plurality of intelligent symbols;
    selecting an X-Y position within the background:
    associating the selected symbol with the X-Y position and an image layer from the plurality of image layers; and
    rendering the background image, wherein rendering the background image includes rendering the plurality of layers superimposed on the background image based on a physical order of the plurality of anatomical layers, and wherein rendering the plurality of layers includes rendering the selected symbol superimposed on the background image based on a rendering order of the plurality of image layers and the plurality of parameters.

2. The method of claim 1, wherein the background image includes a plurality of zones, each zone corresponding to a respective predefined area of the background image.

3. The method of claim 2, wherein the selected symbol is positioned in a zone from the plurality of zones, the zone indicative of an anatomical location.

4. The method of claim 2, wherein the selected symbol is positioned in a zone from the plurality of zones, the method further comprising:
    preventing modification of the selected symbol on a condition that the zone is adapted to prevent modification of the selected symbol; and
    permitting modification of the selected symbol on a condition that the zone is adapted to allow modification of the selected symbol.

5. The method of claim 2, wherein the background image includes a representation of an anatomical structure at an anatomical location, and wherein a zone from the plurality of zones is collocated with the representation of the anatomical structure at the anatomical location, and wherein the representation of the anatomical structure at the anatomical location and the zone are different.

6. The method of claim 2, wherein the X-Y position is within a zone from the plurality of zones, and wherein associating the selected symbol with the X-Y position includes changing the selected symbol based on the zone, wherein changing the selected symbol includes changing a billing code associated with the selected symbol, changing a procedure code associated with the selected symbol, changing a medical treatment associated with a pathological state represented by the selected symbol, or changing text associated with the selected symbol.

7. The method of claim 1, further comprising:
    associating at least one of a standardized billing code or a procedure code with the selected symbol.

8. The method of claim 1, further comprising:
    generating an examination report containing information based on the location of the selected symbol, wherein the examination report includes at least one of the plurality of parameters in a format suitable for submission to a payment provider.

9. The method of claim 1, wherein
    the background image is associated with a scale, and wherein rendering the selected symbol includes rendering the selected symbol proportionally to the background image based on the scale.

10. The method of claim 1, wherein selecting the X-Y position includes identifying the X-Y position based on user input.

11. The method of claim 1, wherein selecting the X-Y position includes identifying the X-Y position based on the plurality of parameters.

12. The method of claim 1, wherein each image layer from the plurality of image layers is associated with a respective set of intelligent symbols from the plurality of intelligent symbols.

13. The method of claim 1, wherein rendering the background image includes rendering the selected symbol superimposed over a second intelligent symbol wherein the image layer associated with the selected symbol corresponds with an anatomical layer having an anatomical order that is greater than an anatomical order of an anatomical layer corresponding to an image layer associated with the second intelligent symbol.

14. The method of claim 1, wherein the plurality of parameters includes a polar symmetry parameter, and wherein associating the selected symbol with the X-Y position includes identifying a location in the background image, the location differing from the X-Y position, and wherein rendering the selected symbol superimposed on the background image includes orienting the selected symbol with respect to the location.

15. The method of claim 1, wherein the plurality of parameters includes a horizontal symmetry parameter or a vertical symmetry parameter, and associating the selected symbol with the X-Y position includes:
    identifying a location in the background image, the location differing from the X-Y position; and
    identifying a second X-Y position within the background, the second X-Y position mirroring the X-Y position with respect to the location; and
    associating a second selected symbol with the second X-Y position, the second selected symbol corresponding to the selected symbol.

16. The method of claim 1, wherein selecting the X-Y position includes:
    identifying a first location within the background image based on user input;
    identifying a second location with the background image based on the plurality of parameters, wherein the first location and the second location differ; and
    selecting the second location as the X-Y position on a condition that the plurality of parameters includes a fixed positioning parameter.

17. The method of claim 16, wherein the fixed positioning parameter is a vertical fixed positioning parameter or a horizontal fixed positioning parameter and wherein the second location indicates a distance from a reference location within the background, wherein the reference location and the first location differ.

18. The method of claim 1, wherein the plurality of parameters includes a density parameter, and wherein rendering the selected symbol superimposed on the background image includes adjusting an appearance of the selected symbol relative to a value of the density parameter.

19. The method of claim 1, wherein the plurality of parameters includes a stage parameter, and wherein the selected symbol includes a plurality of stage symbols, and wherein rendering the selected symbol superimposed on the background image includes rendering one or more stage symbols and omitting one or more stage symbols based on the stage parameter.

20. The method of claim 1, wherein the background image is a first background image, and wherein the selected symbol includes a plurality of selected intelligent symbols and rendering the selected symbol includes rendering each selected intelligent symbol from the plurality of selected intelligent symbols, the method further comprising:
  displaying a second background image representative of the anatomical structure, wherein displaying the second background image includes:
  omitting the first background image; and
  rendering the second background image, wherein rendering the background image includes rendering the plurality of layers superimposed on the second background image based on a physical order of the plurality of anatomical layers, and wherein rendering the plurality of layers includes:
  rendering a first selected intelligent symbol from the plurality of selected intelligent symbols on a condition that the first selected intelligent symbol is associated with a persistence parameter, and
  omitting a second selected intelligent symbol from the plurality of selected intelligent symbols.

\* \* \* \* \*